(12) United States Patent
Briggs, Jr. et al.

(10) Patent No.: US 11,608,787 B2
(45) Date of Patent: Mar. 21, 2023

(54) INTERNAL COMBUSTION ENGINE HAVING CARBON DIOXIDE CAPTURE AND FUEL ADDITIVE SYNTHESIS SYSTEM

(71) Applicant: Southwest Research Institute, San Antonio, TX (US)

(72) Inventors: Thomas E. Briggs, Jr., Helotes, TX (US); Graham Conway, San Antonio, TX (US)

(73) Assignee: SOUTHWEST RESEARCH INSTITUTE, San Antonio, TX (US)

( * ) Notice: Subject to any disclaimer, the term of this patent is extended or adjusted under 35 U.S.C. 154(b) by 18 days.

(21) Appl. No.: 17/446,837

(22) Filed: Sep. 3, 2021

(65) Prior Publication Data

US 2022/0074358 A1 Mar. 10, 2022

Related U.S. Application Data

(60) Provisional application No. 62/706,745, filed on Sep. 8, 2020.

(51) Int. Cl.
*F01N 3/01* (2006.01)
*F02D 19/12* (2006.01)
(Continued)

(52) U.S. Cl.
CPC ....... *F02D 19/0689* (2013.01); *B01D 53/228* (2013.01); *B01D 53/229* (2013.01); *B01D 53/265* (2013.01); *B01D 69/147* (2013.01); *C07C 1/041* (2013.01); *C07C 1/12* (2013.01); *C07C 29/154* (2013.01); *C07C 29/1518* (2013.01); *C10L 1/023* (2013.01); *C10L 1/06* (2013.01); *C10L 10/02* (2013.01); *C10L 10/10* (2013.01); *C25B 1/04* (2013.01); *C25B 9/00* (2013.01); *F01N 3/005* (2013.01); *F01N 3/01* (2013.01); *F01N 3/0892* (2013.01); *F02D 19/0649* (2013.01); *F02D 19/0655* (2013.01); *F02D 19/12* (2013.01); *F02D 35/027* (2013.01); *F02D 41/38* (2013.01); *F02M 25/12* (2013.01);
(Continued)

(58) Field of Classification Search
CPC ......... C07C 1/041; C07C 1/12; C07C 29/154; B01D 53/228; B01D 53/229; B01D 53/265; F01N 3/005; F01N 3/01; F01N 3/0892; F02D 19/0655; F02D 19/12; F02M 25/12; F02M 25/14; C10L 2200/0492; C10L 2290/42
USPC ................................ 123/3, 406.31, DIG. 12
See application file for complete search history.

(56) References Cited

U.S. PATENT DOCUMENTS 6,655,325 B1 * 12/2003 Botti .................. F02B 1/12
429/513
8,454,732 B2 6/2013 Huang et al.
(Continued)

OTHER PUBLICATIONS

"Aramco Debuts Low CO2 Demonstration Truck at SAE Innovations in Mobility Event in Detroit", https://www.saudiaramco.com/en/news-media/news/2019/sae-innovations-mobility-event-detroit, Detroit, MI, 2019.

*Primary Examiner* — Erick R Solis
(74) *Attorney, Agent, or Firm* — Grossman, Tucker, Perreault & Pfleger, PLLC

(57) ABSTRACT

Separation of carbon dioxide from the exhaust of an internal combustion engine, the production of hydrogen from water, and reformation of carbon dioxide and hydrogen into relatively high-octane fuel components.

14 Claims, 1 Drawing Sheet

(51) Int. Cl.

| | |
|---|---|
| *F02M 25/14* | (2006.01) |
| *C07C 1/12* | (2006.01) |
| *F02D 19/06* | (2006.01) |
| *F01N 3/08* | (2006.01) |
| *F01N 3/00* | (2006.01) |
| *F02M 35/10* | (2006.01) |
| *F02M 55/02* | (2006.01) |
| *F02D 41/38* | (2006.01) |
| *B01D 53/22* | (2006.01) |
| *B01D 69/14* | (2006.01) |
| *B01D 53/26* | (2006.01) |
| *C25B 1/04* | (2021.01) |
| *C25B 9/00* | (2021.01) |
| *C07C 29/151* | (2006.01) |
| *C10L 1/06* | (2006.01) |
| *C10L 1/02* | (2006.01) |
| *C10L 10/10* | (2006.01) |
| *C10L 10/02* | (2006.01) |
| *F02D 35/02* | (2006.01) |
| *C07C 29/154* | (2006.01) |
| *C07C 1/04* | (2006.01) |
| *F02M 25/12* | (2006.01) |

(52) U.S. Cl.
CPC ...... *F02M 25/14* (2013.01); *F02M 35/10216* (2013.01); *F02M 55/025* (2013.01); *C10L 2200/0492* (2013.01); *C10L 2270/023* (2013.01); *C10L 2290/42* (2013.01); *F02D 2041/389* (2013.01)

(56) References Cited

U.S. PATENT DOCUMENTS

| | | | |
|---|---|---|---|
| 9,334,204 B1 * | 5/2016 | Radaelli | B01J 8/001 |
| 2013/0333638 A1 * | 12/2013 | Nishida | F02M 23/00 |
| | | | 123/3 |
| 2015/0315507 A1 * | 11/2015 | Camero | C10L 1/18 |
| | | | 44/393 |
| 2016/0017800 A1 * | 1/2016 | Simpson | C25B 1/04 |
| | | | 422/162 |
| 2022/0136119 A1 * | 5/2022 | Flanders | C07C 1/0485 |
| | | | 435/71.1 |
| 2022/0153656 A1 * | 5/2022 | Flanders | C25B 1/23 |
| 2022/0161222 A1 * | 5/2022 | Dahlgren | C10L 1/06 |
| 2022/0178036 A1 * | 6/2022 | Campbell | B01D 67/0093 |
| 2022/0251455 A1 * | 8/2022 | Schuetzle | C25B 1/50 |

* cited by examiner

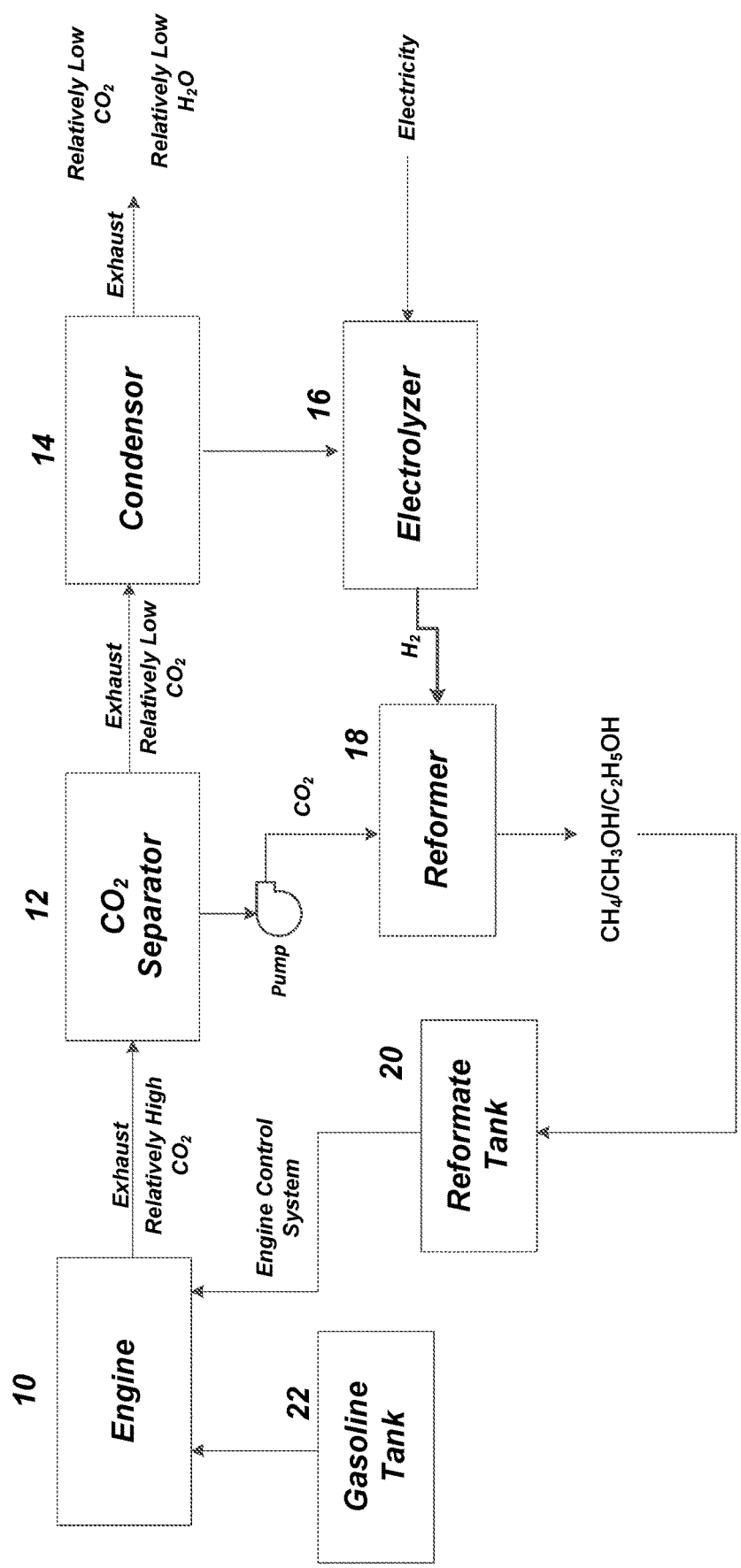

INTERNAL COMBUSTION ENGINE HAVING CARBON DIOXIDE CAPTURE AND FUEL ADDITIVE SYNTHESIS SYSTEM

FIELD

The present invention provides for separation of carbon dioxide from the exhaust of an internal combustion engine, the production of hydrogen from water, and reformation of carbon dioxide and hydrogen into relatively high-octane fuel components.

BACKGROUND

Internal combustion engines continue to be the most economical and practical means of powering road transportation for personal and commercial use. However, societal and regulatory demands are pushing for low- or zero-$CO_2$ emission transportation, which presently means battery electric vehicles. These vehicles are not yet economical for certain applications, can have relatively limited range and utility, and present certain material resource limitations.

There has been some interest and development in making the internal combustion engine a zero-$CO_2$ technology. One path is to use a non-carbon containing fuel such as hydrogen. This can work, but introduces challenges with a lack of fuel availability in the market, packaging of tanks for low-density fuel, and technical difficulties with hydrogen/material interactions. Others have considered onboard carbon dioxide capture and storage systems (example: Saudi Aramco's $CO_2$ capture and storage demonstration truck haps://www.saudiaramco.com/en/news-media/news/2019/sae-innovations-mobility-event-detroit). This approach can yield relatively low $CO_2$ emissions, but requires relatively high energy demand systems for the $CO_2$ separation and storage, and at present cannot capture all of the $CO_2$ emissions. There is also the challenge of what happens to the $CO_2$ as it must be removed from the vehicle and used in a way that does not release it back to the atmosphere.

To satisfy fuel economy and greenhouse gas regulations, engines need to increase in their efficiency but are limited by end-gas knock—the compression ratio of the engine cannot be further increased with existing market fuels due to the octane number of those fuels. If higher octane fuels were available, the engines could be made to be more efficient.

There is also ongoing development of what are termed "advanced combustion engines" that use various methods of controlling the autoignition of the fuel to allow for a kinetically-controlled compression ignition process. These engines offer high potential efficiencies, but are again generally limited in function by the properties of market fuels.

Accordingly, a need remains for an on-board vehicle system that could generate fuel components that would offer relatively higher efficiency potential for internal combustion engine powered vehicles.

SUMMARY

An internal combustion engine comprising an engine control system in communication with the engine that detects and evaluates the presence of engine knock. A carbon dioxide separator is provided to separate carbon dioxide from internal combustion engine exhaust along with a condenser and electrolyzer to separate water from the engine exhaust to provide hydrogen. A reformer is present that converts said separated carbon dioxide and hydrogen into one or more high octane fuel components. The engine control system is configured to introduce the one or more high octane fuel components into the engine upon determination that the engine requires said one or more components to mitigate and/or prevent engine knock.

The present invention also relates to a method of operating an internal combustion engine comprising injecting fuel into a combustion chamber to form an air-fuel mixture and combusting the mixture and forming exhaust gas. One provides a carbon dioxide separator and separates carbon dioxide from the exhaust gas and also separates water from the exhaust gas and converts the water into a supply of hydrogen. The separated carbon dioxide and hydrogen are combined to form one or more high octane fuel components. One then provides an engine control system that detects and evaluates the presence of engine knock and mitigates or prevents engine knock by introducing the one or more high octane fuel components into the internal combustion engine.

BRIEF DESCRIPTION OF THE DRAWING

Embodiments of the present invention are described in detail below with reference to the attached drawing FIGURE wherein:

FIG. 1 is a block diagram of the vehicle-integrated carbon dioxide capture and fuel additive synthesis system.

DETAILED DESCRIPTION OF THE DRAWING

The present invention provides for separation of carbon dioxide ($CO_2$) from the exhaust of an internal combustion engine, the production of hydrogen from water via use of an electrolyzer, and the reformation of carbon dioxide and hydrogen into one or more relatively high-octane fuel components. The one or more relatively high octane fuel components may then be fed to the engine as required, via use of an engine control system (ECS) that evaluates engine performance. The ECS preferably evaluates, among other things, the knocking behavior of the engine which then responds by introducing the one or more relatively high octane fuel components into the engine fuel to, among other things, mitigate or reduce the identified knocking (combustion of the air/fuel mixture that does not result from propagation of the flame front).

Attention is directed to FIG. 1 which illustrates a preferred embodiment of the present invention. The internal combustion engine 10 output exhaust as illustrated is relatively high in $CO_2$ content. Such exhaust is then preferably passed through a $CO_2$ separator 12 where the $CO_2$ removed from the exhaust can be pumped into a reformer 18. The $CO_2$ separator 12 preferably relies upon a membrane separation of $CO_2$ from the mixture of exhaust gases.

Such membrane may preferably be in tubular form and include a substrate layer comprising inorganic oxides, a barrier layer of in-situ formed $Li_2ZrO_3$, a $Li_2ZrO_3$ sorbent layer and an inorganic oxide cap layer. The substrate layer of inorganic oxides are preferably of average pore size 3.0 μm to 10.0 μm which is 20-80% porous with a thickness of 6.0 mm to 15.0 mm. One may then deposit on the substrate layer precursors for the formation of $Li_2ZrO_3$ and react the precursors for the formation of a $Li_2ZrO_3$ barrier layer wherein the barrier layer is formed at a thickness of 10 μm to 100 μm with a porosity of 0% to 30%. One may then deposit on the barrier layer a sorbent layer comprising $Li_2ZrO_3$ at a thickness of 100 μm to 500 μm followed by deposition of a cap layer on the sorbent layer comprising inorganic oxides. The cap layer has a thickness of 50 μm to 250 μm. One may then expose such membrane to carbon dioxide at elevated temperatures (400° C. to 700° C.) and separate carbon dioxide from the exhaust gas mixture. Reference is made to U.S. Pat. No. 8,454,732 whose teachings are incorporated by reference.

Continuing, the exhaust that emerges from the $CO_2$ separator 12 is relatively low in $CO_2$ content and is then introduced to a condenser 14 which removes water where the water is introduced into electrolyzer 16. The electrolyzer 16 receives electricity, which may preferably be electricity from the vehicle battery system. The electrolyzer 16 therefore initiates electrolysis of water and provides for the decomposition of water into oxygen and hydrogen. The hydrogen gas so produced is then introduced to reformer 18, which as noted above, also receives $CO_2$ from the $CO_2$ separator 12.

Reformer 18 therefore provides for the reaction of carbon dioxide with hydrogen to form one or more relatively high octane fuel components. The high octane fuel components are understood herein to be any components that when added to engine fuel (e.g. gasoline), serve to increase the octane rating. Such components preferably include methane ($CH_4$), methanol ($CH_3OH$) and/or ethanol ($C_2H_5OH$). Accordingly, the reformer 18 combines $CO_2$ and $H_2$ in the presence of a catalyst, and under elevated temperature and pressure, to generate hydrocarbon products that increase, as noted, the octane rating of any available fuel. Multiple catalyst formulations are preferred for such purpose. The preferred catalysts can be $Cu/ZnO/Al_2O_3$ or $Ni_5Ga_3$. With these preferred catalysts, the reformation reactions will occur at preferred temperatures from 200° C. to 300° C. and under preferred pressures ranging from 0.1 to 8 MPa. Depending on the specific details of the catalyst and reformation conditions, at least 50% of the $CO_2$ and $H_2$ will be preferably converted into $CH_4$, $CH_3OH$, and $C_2H_5OH$. The methane, methanol and/or ethanol so produced may then be conveniently stored in reformate tank 20.

The engine control system (ECS) preferably utilizes a processor along with a map-based control strategy with feedback to detect, evaluate and then determine when and in what quantity to introduce the high-octane fuel components to the engine. Based on a combination of one or more of such factors such as engine speed, manifold temperature, throttle pedal position, the ECS can determine that the engine requires the high-octane fuel components (e.g., $CH_4$, $CH_3OH$, and/or $C_2H_5OH$) to mitigate and/or prevent knock from occurring. The components will then be injected according to the calibrated tables in the controller, with the gasoline injection command adjusted to maintain the engine at a steady load condition. Feedback will preferably be through an engine knock sensor where the sensor signal can be used both to command a spark timing retard for knock control and/or an increased injection rate of the relatively high octane components, within limits that can be defined in the ECS maps.

Expanding on the above, the relatively high-octane fuel delivery can be accomplished in multiple preferred manners to satisfy a specific engine's design and performance requirements. Gaseous components such as $CH_4$ can be introduced through a metering valve or injector in the engine intake system after any supercharging devices. The engine intake system may be understood as the system that allows air and fuel into the engine. The liquid components (e.g. methanol or ethanol) can also preferably be metered into the fuel rail that supplies the fuel injectors. This induces a delay between the command of high octane fuel delivery and the engine receiving the fuel into the combustion chamber but is a practical approach. For more direct timing control, it is contemplated that the relatively high octane fuel components can be supplied to a secondary set of fuel injectors located in the intake ports or directly into the combustion chamber dedicated to the delivery of the high octane fuel components. This approach would provide immediate delivery of the high octane fuel components upon a command from the ECS.

Among other contemplated benefits of the present invention include reduced $CO_2$ emissions as the $CO_2$ is captured and recycled into a fuel component. In addition, the present invention is contemplated to increase the efficiency of the engine as the compression ratio can be increased. In addition, it is contemplated that the present invention will provide relatively higher fuel economy resulting in higher miles driven per gallon of utilized fuel.

The foregoing description of several methods and preferred embodiments have been presented for illustration and is not intended to be exhaustive or limit the scope of the invention as may be recited in the claims.

The invention claimed is:

1. An internal combustion engine comprising:
   an engine control system in communication with said engine that detects and evaluates the presence of engine knock;
   a carbon dioxide separator to separate carbon dioxide from internal combustion engine exhaust;
   a condenser and electrolyzer to separate water from said engine exhaust and provide hydrogen;
   a reformer that converts said separated carbon dioxide and hydrogen into one or more high octane fuel components;
   wherein said engine control system is configured to introduce said one or more high octane fuel components into said engine upon determination that said engine requires said one or more components to mitigate and/or prevent engine knock.

2. The internal combustion engine of claim 1, wherein said carbon dioxide separator comprises a substrate layer of inorganic oxides, a barrier layer of in-situ $Li_2ZrO_3$, a $Li_2ZrO_3$ sorbent layer and an inorganic oxide cap layer.

3. The internal combustion engine of claim 1, wherein reformer converts said separated carbon dioxide and hydrogen into a mixture of methane, methanol and ethanol.

4. The internal combustion engine of claim 1, wherein said reformer comprises a catalyst selected from Cu, ZnO, $Al_2O_3$ or $Ni_5Ga_3$.

5. The internal combustion engine of claim 1, wherein said engine includes an intake system and said high octane components are configured to be introduced into said intake system.

6. The internal combustion engine of claim 1, wherein said engine includes a fuel rail that supplies fuel injectors wherein said one or more high octane components are configured to be introduced to said fuel rail.

7. The internal combustion engine of claim 1, having fuel injectors dedicated to delivery of said one or more high octane fuel components.

8. A method of operating an internal combustion engine comprising:
   injecting fuel into a combustion chamber to form an air-fuel mixture and combusting said mixture and forming exhaust gas;
   providing a carbon dioxide separator and separating carbon dioxide from said exhaust gas;
   separating water from said exhaust gas and converting said water into a supply of hydrogen;

combining said separated carbon dioxide and hydrogen and forming one or more high octane fuel components;

providing an engine control system that detects and evaluates the presence of engine knock;

mitigating or preventing engine knock by introducing said one or more high octane fuel components into said internal combustion engine.

9. The method of claim 8, wherein said carbon dioxide separator comprises a substrate layer of inorganic oxides, a barrier layer of in-situ $Li_2ZrO_3$, a $Li_2ZrO_3$ sorbent layer and an inorganic oxide cap layer.

10. The method of claim 8, wherein said one or more high octane fuel components comprise a mixture of methane, methanol and ethanol.

11. The method of claim 8 wherein carbon dioxide and hydrogen are combined in the presence of a catalyst selected from Cu, ZnO, $Al_2O_3$ or $Ni_5Ga_3$.

12. The method of claim 8, wherein said engine includes an intake system and said one or more high octane components are configured to be introduced into said intake system.

13. The method of claim 8, wherein said engine includes a fuel rail that supplies fuel injectors wherein said one or more high octane components are configured to be introduced to said fuel rail.

14. The method of claim 8, wherein said engine has fuel injectors dedicated to delivery of said one or more high octane fuel components.

* * * * *